US009687440B2

(12) United States Patent
Lyga et al.

(10) Patent No.: US 9,687,440 B2
(45) Date of Patent: *Jun. 27, 2017

(54) CGRP COMPOSITIONS AND USES THEREOF

(71) Applicant: Avon Products, Inc., Suffern, NY (US)

(72) Inventors: John W. Lyga, Basking Ridge, NJ (US); Laurence Dryer, Long Beach, CA (US)

(73) Assignee: Avon Products, Inc, Rye, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/669,545

(22) Filed: Mar. 26, 2015

(65) Prior Publication Data

US 2015/0196483 A1    Jul. 16, 2015

Related U.S. Application Data

(63) Continuation of application No. 12/648,581, filed on Dec. 29, 2009, now abandoned.

(51) Int. Cl.
| | |
|---|---|
| *A61K 36/48* | (2006.01) |
| *A61K 8/97* | (2017.01) |
| *A61K 8/44* | (2006.01) |
| *A61K 8/49* | (2006.01) |
| *A61Q 19/08* | (2006.01) |

(52) U.S. Cl.
CPC ............... *A61K 8/975* (2013.01); *A61K 8/44* (2013.01); *A61K 8/49* (2013.01); *A61K 8/494* (2013.01); *A61K 8/4973* (2013.01); *A61K 8/97* (2013.01); *A61Q 19/08* (2013.01)

(58) Field of Classification Search
CPC ........ A61K 36/00; A61K 36/06; A61K 36/15; A61K 36/81; A61K 36/82
USPC ........... 424/725, 195.16, 770, 775, 760, 777
See application file for complete search history.

(56) References Cited

U.S. PATENT DOCUMENTS

| | | | |
|---|---|---|---|
| 6,048,855 A | 4/2000 | De Lacharriere et al. | |
| 6,099,854 A | 8/2000 | Howard et al. | |
| 6,103,241 A | 8/2000 | Hood | |
| 6,146,640 A | 11/2000 | Dyke | |
| 6,630,467 B2 | 10/2003 | O'Neill | |
| 7,592,024 B1 | 9/2009 | Ptchelintsev et al. | |
| 7,618,662 B2 | 11/2009 | Hines et al. | |
| 7,846,483 B2 * | 12/2010 | Montanari ............... | A61K 8/14 424/722 |
| 8,128,914 B2 | 3/2012 | Ptchelintsev et al. | |
| 8,168,212 B2 * | 5/2012 | Ptchelintsev et al. ........ | 424/401 |
| 8,221,766 B2 | 7/2012 | Dryer et al. | |
| 8,394,427 B2 | 3/2013 | Zheng et al. | |
| 8,512,764 B2 | 8/2013 | Paufique | |
| 8,771,758 B2 | 7/2014 | Ptchelintsev | |
| 9,034,396 B2 | 5/2015 | Zheng et al. | |
| 9,066,896 B2 | 6/2015 | Zheng et al. | |
| 9,186,316 B2 | 11/2015 | Khusial et al. | |
| 9,238,000 B2 | 1/2016 | Khusial et al. | |
| 2002/0183248 A1 | 12/2002 | Oldham et al. | |
| 2003/0207818 A1 | 11/2003 | Jia et al. | |
| 2004/0028643 A1 | 2/2004 | Chiba et al. | |
| 2005/0136028 A1 | 6/2005 | Ptchelintsev | |
| 2005/0164957 A1 | 7/2005 | Jia et al. | |
| 2005/0271751 A1 | 12/2005 | Perrier et al. | |
| 2006/0134231 A1 | 6/2006 | Hines et al. | |
| 2006/0204471 A1 | 9/2006 | Lacharriere et al. | |
| 2007/0224272 A1 | 9/2007 | Touitou | |
| 2008/0221003 A1 | 9/2008 | Meine et al. | |
| 2008/0274453 A1 | 11/2008 | Hageman | |
| 2009/0028895 A1 * | 1/2009 | Smith .................. | A61K 31/045 424/195.15 |
| 2009/0221542 A1 | 9/2009 | Wang et al. | |
| 2010/0158828 A1 | 6/2010 | Ptchelintsev et al. | |
| 2011/0124719 A1 | 5/2011 | Kim et al. | |
| 2012/0003332 A1 | 1/2012 | Zheng et al. | |
| 2013/0053423 A1 | 2/2013 | Lyga | |
| 2013/0102606 A1 | 4/2013 | Hwang et al. | |
| 2013/0149268 A1 | 6/2013 | Chen et al. | |

(Continued)

FOREIGN PATENT DOCUMENTS

| | | |
|---|---|---|
| CN | 101039579 A | 9/2007 |
| CN | 101559033 A | 10/2009 |

(Continued)

OTHER PUBLICATIONS

Harada et al. "Effect of topical application of capsaicin and its related compounds on dermal insulin-like growth factor-I levels in mice and on facial skin elasticity in humans", Growth Hormone & IGF Research 17 (2007) 171-176.*
Wang et al. "Specific Inhibition of Cyclic AMP-Dependent Protein Kinase by Warangalone and Robustic Acid", Phytochemistry, vol. 44, No. 5, pp. 787-796.*
http://en.wikipedia.org/wiki/Melicope (2015).
U.S. Appl. No. 13/395,682, filed Mar. 13, 2012, Ptchelintsev et al.
U.S. Appl. No. 13/602,557, filed Sep. 4, 2012, Zheng et al.
U.S. Appl. No. 13/158,947, filed Jun. 13, 2011, Zheng et al.

(Continued)

*Primary Examiner* — Chris R Tate
*Assistant Examiner* — Deborah Davis
(74) *Attorney, Agent, or Firm* — Brian P McCloskey

(57) ABSTRACT

Compositions comprising at least one ingredient that stimulates, enhances, or increases CGRP expression, and a physiologically- or cosmetically-acceptable vehicle. The ingredient may be a compound, natural ingredient, such as a plant or fungus, derivatives, analogs, mimetics, synthetics and the like that stimulates CGRP expression. The CGRP plant includes plants, plant materials, plant extracts, synthetics, or combinations thereof that stimulate CGRP expression. The disclosure is also directed to methods of using the CGRP compositions for decreasing, reducing, or inhibiting fine lines or wrinkled skin.

2 Claims, No Drawings

(56) References Cited

U.S. PATENT DOCUMENTS

| | | | |
|---|---|---|---|
| 2013/0149397 A1 | 6/2013 | Chen et al. | |
| 2014/0255523 A1 | 9/2014 | Ptchelintsev et al. | |

FOREIGN PATENT DOCUMENTS

| | | | | |
|---|---|---|---|---|
| FR | 2902656 A1 | * | 12/2007 | ............... A61K 8/97 |
| JP | 48022638 B | * | 7/1973 | |
| JP | H3-14596 A | | 1/1991 | |
| JP | H3-27318 A | | 2/1991 | |
| JP | H5-58874 A | | 3/1993 | |
| JP | H5-317016 A | | 12/1993 | |
| JP | H10-17460 A | | 1/1998 | |
| JP | H11-92331 A | | 6/1999 | |
| JP | H11-246337 A | | 9/1999 | |
| JP | 200095663 A | | 4/2000 | |
| JP | 2000505809 A | | 5/2000 | |
| JP | 2000178168 A | | 6/2000 | |
| JP | 2000297291 A | | 10/2000 | |
| JP | 2000302634 A | | 10/2000 | |
| JP | 2001506579 A | | 5/2001 | |
| JP | 2001163754 A | * | 6/2001 | |
| JP | 20012575 A | | 9/2001 | |
| JP | 2001278783 A | | 10/2001 | |
| JP | 2002087973 A | | 3/2002 | |
| JP | 2002179581 A | | 6/2002 | |
| JP | 2003113027 A | | 4/2003 | |
| JP | 20032820 A | | 8/2003 | |
| JP | 2003342184 A | | 12/2003 | |
| JP | 200451492 A | | 2/2004 | |
| JP | 2004331635 A | | 11/2004 | |
| JP | 2005343884 A | | 12/2005 | |
| JP | 2006069954 A | | 3/2006 | |
| JP | 200695182 A | | 4/2006 | |
| JP | 2007291031 A | | 11/2007 | |
| JP | 200913128 A | | 1/2009 | |
| JP | 2009523730 A | | 6/2009 | |
| JP | 2009197035 A | | 9/2009 | |
| JP | 2009221116 A | | 10/2009 | |
| JP | 2010500282 A | | 1/2010 | |
| JP | 2010090069 A | | 4/2010 | |
| WO | 2006068778 A2 | | 6/2006 | |
| WO | 2007045060 A1 | | 4/2007 | |
| WO | 2007093839 A1 | | 8/2007 | |
| WO | 2009048282 A2 | | 4/2009 | |
| WO | 2009134404 A2 | | 11/2009 | |
| WO | 2012005872 A1 | | 1/2012 | |

OTHER PUBLICATIONS

U.S. Appl. No. 13/305,779, filed Nov. 29, 2011, Zheng et al.
U.S. Appl. No. 13/808,280, filed Jan. 4, 2013, Hwang et al.
U.S. Appl. No. 14/335,467, filed Jul. 18, 2014, Lyga et al.
U.S. Appl. No. 13/710,617, filed Dec. 11, 2012, Zheng, Qian et al.
U.S. Appl. No. 13/602,557, filed Sep. 4, 2012, Zheng, Qian et al.
U.S. Appl. No. 13/158,947, filed Jun. 13, 2011, Zheng, Qian et al.
U.S. Appl. No. 13/305,779, filed Nov. 29, 2011, Zheng, Qian et al.
U.S. Appl. No. 14/284,869, filed May 22, 2014, Ptchelintsev, Dmitri.
U.S. Appl. No. 13/216,626, filed Aug. 24, 2011, Thorn Leeson, Daniel.
U.S. Appl. No. 13/710,536, filed Dec. 11, 2012, Hwang, Cheng et al.
U.S. Appl. No. 14/066,862, filed Oct. 30, 2013, Lyga, John W. et al.
U.S. Appl. No. 14/055,037, filed Oct. 16, 2013, Khusial, Permanan Raaj.
U.S. Appl. No. 12/648,581, filed Dec. 29, 2009, Lyga et al.
U.S. Appl. No. 14/661,061, filed Mar. 18, 2015, Khusial et al.
Han et al., "TGF-alpha 1 up-regulates paxillin protein expression in malignant astrocytoma cells: requirement for a fibronectin substrate," Oncogene, vol. 20, pp. 7976-7986 (2001).
Maggi, et al, Multiple mechanisms in the smooth muscle relaxant action of calcitonin gene-related peptide (CGRP) in the guinea-pig ureter Naunyn-Schmiedeberg's Arch Pharmacol., 1994, vol. 350, pp. 537-547. p. 537, col. 2, para 3; p. 538, col. 1, para 2; p. 539, Table 1.
Choi, Eun-Mi et al., "Screening of Indonesian medicinal plants for inhibitor activity on nitric oxide production of RAW264.7 cells and antioxidant activity," Fitoterapia, vol. 76, pp. 194-203 (2005).
Fujimoto, Norihiro et al., "Expression of microfibril-associated glycoprotein-1 (MAGP-1) in human epidermal keratinocytes," Arch. Dermatol. Res. vol. 292, pp. 21-26 (2000).
Jothi, G. J. et al., "Glimpses of Tribal Botanical Knowledge of Tirunelveli Hills, Western Ghats, India," Ethnobotanical Leaflets, vol. 12, pp. 118-126 (2008).
Micor, Jose Rene L. et al., "Biological Activity of Bignay [*Antidesma bunius* (L.) Spreng] Crude Extract in Artemia salina," J. Med. Sci., vol. 5, No. 3, pp. 195-198 (2005).
Mintel, "Treatment Cream," Database GNPD [online], database accession No. 1646948 (2011).
Tatano, Yutaka et al., "Significant Decrease in Tropoelastin Gene Expression in fibroblasts from a Japanese Costello Syndrome Patient with Impaired Elastogenesis and Enhanced Proliferation," J. Biochem., vol. 140, pp. 193-200 (2000).
Revilla, Eugenio et al., "Comparison of Several Procedures Used for the Extraction of Anthocyanins from Red Grapes," J. Agric. Food Chem., vol. 46, pp. 4592-4597 (1998).
Barrows et al., "Anti-TB activity of Evodia elleryana bark extract," Fitoterapia, vol. 78, No. 3, pp. 250-252 (2007).
Jones et al., "Essential Oils from the Queensland," Department of Chemistry, vol. 1, No. 27, pp. 1-7 (1946).
Khan et al., "Antimicrobial activity of Evodia elleryana," Fitoterapia, vol. 71, pp. 72-74 (2000).
Weinbaum et al., "Deficiency in Microfibril-associated Glycoprotein-1 Leads to Complex Phenotypes in Multiple Organ Systems*," Journal of Biological Chemistry, vol. 283, No. 37, pp. 25533-25543 (2008).
Kang, Sewon et al., "Topical N-Acetyl Cysteine and Genistein Prevent Ultraviolet-Light-Induced Signaling That Leads to Photoaging in Human Skin in vivo," The Society for Investigative Dermatology, Inc,; vol. 120, No. 5, pp. 835-841 (2003).
Nanasombat, S. et al., "Antimicrobial, antioxidant and anticancer activities of Thai local vegetables," Journal of Medicinal Plants Research, vol. 3, No. 5, pp. 443-449 (2009).
Singthong, Jittra et al., Extraction and physicochemical characterisation ofpolysaccharide gum from Yanang (*Tiliacora triandra*) leaves, Food Chemistry, vol. 114, pp. 1301-1307 (2009).

* cited by examiner

CGRP COMPOSITIONS AND USES THEREOF

CROSS-REFERENCE TO RELATED APPLICATIONS

This application is a continuation of, and claims priority to, U.S. patent application Ser. No. 12/648,581 filed on Dec. 29, 2009, the entirety of which is incorporated by reference in its entirety.

TECHNICAL FIELD

The instant disclosure relates generally to compositions for administration to skin having fine lines and/or wrinkles. More specifically, these compositions contain ingredients that stimulate, increase or elevate expression of calcitonin gene-related peptide (CGRP). The disclosure is also directed to the use of such compositions for application to fine lines and/or wrinkles typically found in aged, aging, or environmentally damaged skin.

BACKGROUND

The cosmetics industry is constantly developing products to improve the condition and appearance of skin, particularly skin that gradually develops fine lines, wrinkles, or deeper creases and folds due to damage and aging. Consumers increasingly demand the youthful look. They seek products that mitigate or delay the dermatological signs of chronologically- or hormonally-aging skin, as well as skin aging due to environmental stress, such as fine lines, wrinkles, sagging skin and other conditions due to a progressive loss of cell growth, proliferation and functionality in the epidermal and dermal skin layers. During the aging process, the complexion of the skin, i.e., the color and appearance of the skin, deteriorates slowly either from aging and/or intrinsic or extrinsic factors. For example, premature aging and wrinkling of the skin may be accelerated by excessive exposure to the sun and other damaging elements, frequent use of tobacco products, overactive facial expression muscles, poor nutrition, or skin disorders. Numerous cosmetic and medical treatments have been developed in an attempt to treat environmentally damaged, aging or aged skin. However, such cosmetics or treatments commonly contain harsh ingredients or components that are frequently associated with consumer discomfort, such as burning, itching, and redness. Invasive techniques are available to reduce the appearance of fine lines, wrinkles, or skin folds; however, but these are often risky and require the supervision or assistance of a physician, which can be inconvenient and costly. While historically, non-invasive treatments have had only minimal success. Regardless of the cause of facial creases or folds, safe and effective treatments for reduction or elimination of these problems have been exceedingly difficult to achieve.

Sensitive skin was found to involve the release of neuropeptides from nerve fibers. One such neuropeptide is Calcitonin Gene-Related Peptide (CGRP) which originates from epidermal and dermal nerve endings. Therefore, scientists have searched for CGRP antagonists to reduce the release of these neuropeptides which are associated with respiratory, inflammatory, allergy, and dermatological diseases, disorders and conditions. For example, the dermatological conditions include eczema or prurigo. Similar to neuropeptides, neurotransmitters are endogenous chemicals which relay, amplify, and modulate signals between, for example, a neuron and a cell. One type of neurotransmitter is acetylcholine which is inclined to cause excitatory actions in the central nervous system. However, in the peripheral nervous system, acetylcholine activates muscles, and is a transmitter at the neuromuscular junction connecting motor nerves to muscles.

Botulinum toxin is a neurotoxic protein produced by the bacterium *Clostridium botulinum*, and is believed to be the most toxic substance presently known. Botulism is a type of food poisoning when a neurotoxin from *Clostridium botulinum* is ingested, such as botulinum toxin A. Basically, the botulinum toxins block the signals that normally instruct your muscles to contract. Botox® is a trade name for botulinum toxin A and is commonly used in cosmetic procedures to reduce or eliminate the appearance of wrinkles.

However, one of the disadvantages of using Botox® is that the administration must be an injection administered directly to the desired location. injections are inconvenient and in view of the lethality of botulinum toxin, must be administered by an experienced or trained person. Moreover, oftentimes there is bruising at the injection site which may last about 7-10 days. Other adverse effects of Botox® when used for cosmetic purposes include, but are not limited to, headaches, focal facial paralysis, muscle weakness, dysphagia, flu-like syndromes, and allergic reactions.

There remains a need for compositions which effectively reduce signs of aging without any or limited negative side effects. As a result, consumers seek convenient, effective and preferably natural compositions that do not cause discomfort, burning, itching, and other unwanted side effects. Active ingredients and components derived from plants and plant seeds have commonly been employed for a myriad of medicinal, therapeutic and cosmetic purposes.

Thus, there is a general need in the cosmetics industry for products that retard or counter the aging effects on the skin, and more specifically for products that produce such effects without undesirable side effects. In particular, there remains a need for compositions that have anti-aging and skin texture benefits using, for example, natural materials, such as but not limited to plants or fungi, as active components.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY

It is an object of the disclosure to provide novel compositions that counter the effects of aged, aging, or damaged skin which is defined herein as skin having the appearance of aged skin. More specifically, the composition disclosed herein is a Calcitonin Gene-Related Peptide (CGRP)-stimulating composition, or CGRP composition, comprising an ingredient that stimulates, enhances, or increases CGRP expression and a physiologically- and/or cosmetically-acceptable carrier, vehicle, or diluent. The ingredient that stimulates CGRP expression, or CGRP ingredient, may be a chemical compound, a natural ingredient, synthetics, mimetics, analogs, or homologs thereof.

Another object of the disclosure is directed to a CGRP composition comprising a natural ingredient that stimulates expression of CGRP, and a physiologically- and/or cosmetically-acceptable carrier, vehicle, or diluent. The natural ingredient is a CGRP natural ingredient which stimulates expression of CGRP. The CGRP natural ingredient may be a fungus, plant, or combinations thereof. The CGRP plant may be the whole plant, part of the plant, extracts of the plant, and the like.

It is a further object of the disclosure to provide methods of improving the overall appearance of aged or damaged skin or various signs of intrinsic aging and photo-aging of skin, by treating, reversing, and/or reducing signs of aging, such as fine lines or wrinkles, by applying the disclosed CGRP composition. In yet a further object, the CGRP composition is applied as a prophylactic to skin that has fine lines or is prone to wrinkles.

Another object of the method is directed to a method of imparting an anti-aging benefit to skin comprising topically applying to skin in need thereof a CGRP composition in an amount sufficient to inhibit or block muscle cell contraction or the acetylcholine signaling pathway, to relax muscles, or to reduce the severity of fine lines and/or wrinkles.

In yet a further object of the disclosure, a method of treating fine lines and/or wrinkles on skin is provided, comprising topically applying to the fine lines and/or wrinkles on the skin in need thereof a CGRP composition comprising an effective amount of a CGRP compound, a CGRP natural ingredient, or combinations thereof, in a physiologically- and/or cosmetically-acceptable carrier, vehicle, or diluent for a time sufficient to treat and reduce the appearance of the fine lines or wrinkles of the skin.

These and other objects of the present disclosure will become apparent to those skilled in the art after a reading of the following detailed description, including the illustrative embodiments and examples.

DETAILED DESCRIPTION

The present disclosure provides novel compositions and their methods of use for effectively treating signs of aging, such as dermatological aging, or the appearance of aging skin resulting from skin damage, diseases, disorders or conditions that may cause or induce such an appearance, including but not limited to fine lines, creases, wrinkles, furrows, sagging skin, skin folds, and the like. These signs are due to, for example, chronological aging, hormonal aging and/or photo-aging. The disclosed CGRP composition described herein improves the aesthetic appearance of skin. It is to be understood that chronological aging represents the structural, functional, and metabolic changes in the skin that parallel the aging and degenerative change in other body organs, whereas photo-aging is a separate process and largely involves damage to the skin due to an exposure to environment such as the sunlight. Improvements in the aesthetic appearance of the skin may be achieved by administering these compositions to age-affected skin on a regular and consistent basis such as daily basis.

It is to be understood that, as used herein, the terms treating and treatment include and encompass reducing, ameliorating, improving, alleviating, and/or eliminating the dermatological effects of aging and/or environmental stress. The present or inventive compositions and methods are suitable for use in treating dermatological conditions of the skin in numerous areas of the body, including, without limitation, the face, forehead, lips, neck, arms, hands, legs, knees, feet, chest, back, buttocks, and the like. However, treatment may occur wherever the reduction of fine lines or wrinkles is desired. In one embodiment, the composition is a face composition that is applied to the face and surrounding areas, including the jaw line and neck. Another embodiment may be directed to the topical application of the composition to the hands.

The instant disclosure is directed to a composition that reduces or inhibits the effects of dermatological aging and uses thereof. The term "wrinkle" or "wrinkling" refers to both fine wrinkling and coarse wrinkling. Fine wrinkling or fine lines refers to superficial lines and wrinkles on the skin surface. Coarse wrinkling refers to deep furrows or creases, particularly deep lines/wrinkles on the face and around the eyes, including expression lines such as frown lines and wrinkles, forehead lines and wrinkles, crow's feet lines and wrinkles, nasolabial fold and marionette lines and wrinkles. Forehead lines and wrinkles refer to superficial lines and/or deep furrows on skin of the forehead. Crow's feet lines and wrinkles refer to superficial lines and/or deep furrows on skin around the eye area. Marionette lines and wrinkles refer to superficial lines and/or deep furrows on skin around the mouth. Wrinkles can be assessed for number, length, and depth of the lines.

It has surprisingly been found that Calcitonin Gene-Related Peptide (CGRP) expression results in relaxation of muscles or the inhibition of contracting muscles. Without wishing to be bound by any particular theory, CGRP is believed to block acetylcholine (ACh) from interacting with the acetylcholine receptor. Normally, the interaction between ACh and its receptor, i.e., ACh receptor, results in a signal for muscles to contract. However, it is believed that CGRP interferes with ACh from binding to its ACh receptor. Interference may occur possibly by any means, such as but not limited to, blocking the release of ACh, blocking the ACh signaling pathway, or CGRP oversaturation or competition with ACh for binding to the ACh receptor. Regardless of the mechanism of action, CGRP is expressed in an amount sufficient to interfere with muscle contraction, thereby resulting in relaxed muscles which reduce the appearance of fine lines or wrinkles. The presence or increase of CGRP expression modulates signaling such that muscles do not contract, thereby contributing to the appearance of decreased skin aging as embodied by fine lines, wrinkles, and the like. In view of these findings and others, the disclosed composition comprising a CGRP expression stimulator or CGRP ingredient is contemplated to be useful in combating signs of skin damage and skin aging, including reducing fine lines and wrinkles, skin sagging or atrophy, loss of elasticity, discoloration of skin, and related signs of aging in skin through blocking muscle contraction.

Accordingly, in an embodiment of the disclosure, CGRP compositions comprising a CGRP ingredient, such as but not limited to a CGRP compound, a CGRP natural ingredient, or continuations thereof, that stimulates the expression of CGRP is useful in enhancing and improving the aesthetic appearance of skin having fine lines, wrinkles, furrows and the like, by reducing or blocking muscles from contracting. CGRP natural ingredients includes any natural ingredient, fungus, botanical, tree, plant, or combinations thereof, that stimulates, increases or enhances CGRP expression. For example, a CGRP plant is any plant, plant part, or plant extract that stimulates, increases or enhance CFRP expression.

One embodiment of the disclosure is directed to a CGRP composition, comprising at least one ingredient that stimulates the expression of CGRP and a physiologically- or cosmetically-acceptable carrier. CGRP or a CGRP ingredient is defined herein as at least one stimulator of CGRP expression. The CGRP compound may be a synthetic, a mimetic, or a derivative that functions similarly to or has similar activity to a CGRP compound. CGRP expression may be identified and isolated by performing binding and enzyme assays. For example, assays utilizing the CGRP receptor and testing various compounds that bind the receptor. Receptor-ligand binding assays and enzyme immunoassays may be utilized. See Example 1 for the specific method utilized for identifying CGRP expression. Example 2 provides exemplary CGRP compositions.

A further embodiment of the disclosure is directed to a CGRP composition comprising a compound that stimulates CGRP expression, i.e., CGRP compound. Examples of compounds that stimulate, increase, or enhance CGRP expression include but are not limited to L-4-thiazolylalanine, tetramethylpyrazine, (2S,3S)-3-amino-2-hydroxy-4-phenylbutanoic acid, 3-Hydroxy-4,5-dimethylfuran-2(5H)-one, and synthetics, derivatives, analogs, and homologs thereof, and combinations thereof. The disclosed composition may have a CGRP ingredient of CGRP compounds, CGRP natural ingredients, or combinations thereof.

In a further embodiment of the disclosure, any natural ingredient that stimulates CGRP activity as determined by methods commonly known and used in the art may be utilized in the inventive composition. Non-limiting examples of useful botanicals and fungi that stimulate CGRP expression in the disclosed composition include: black cohosh (*Cimicifuga racemosa*), *Capsicum amuum*, cedar, *Derris Scandens* Benth, *Erythrina flabelliformis*, *Withania somnifera*, fir needle (*Abies alba*), *Helichrysum gymnocephalum*, holly (*Ilex*), laurel clock vine (*Thunbergia laurifloria*), *Leptospermum lanigerum*, *Grifola frondosa*, *Melicope hayesii*, norway spruce, *Phyllarthron bojeranum*, pine needles, *Piper nigrum*, *Sophora tomentosa*, spruce needles, *Thuja*, or combinations thereof.

A further embodiment of the disclosure is directed to a composition comprising a natural ingredient that stimulates CGRP expression, such as but not limited to *Capsicum amuum*, *Derris Scandens* Benth, *Erythrina flabelliformis*, *Helichrysum gymnocephalum*, *Thunbergia laurifloria*, *Leptospermum lanigerum*, *Melicope hayesii*, *Phyllarthron bojeranum*, *Piper nigrum*, *Sophora tomentosa*, or combinations thereof. One embodiment of the disclosure is directed to any of the CGRP plants, either whole, part, or extracts, or combinations thereof, for use in the CGRP compositions of the disclosure. CGRP ingredients are incorporated into the compositions of the disclosure in a variety of forms. The CGRP ingredient may be in a pure form, a semi-pure form, unpurified form, a solid or liquid extract or derivative, or a solid natural plant material. For example, *Erythrina flabelliformis* or *Sophora tomentosa* may be in the form of a liquid, a semi-solid, or a solid. In one embodiment, the botanical component is an essential oil.

Another embodiment relates to a plant that stimulates the expression of CGRP. Plants that stimulate the expression of CGRP, also referred to herein as CGRP plants, include the entire plant or various parts and forms of the plant, such as flowers, leaves, fruit, pods, beans, seeds, needles, roots, bark, cones, stems, rhizomes, callus cells, protoplasts, organs and organ systems, and meristems. Any one of the above plant materials that stimulate CGRP expression may be incorporated into a CGRP composition, such as but not limited to, whole, minced, ground or crushed, extract or otherwise physically modified for incorporation into the composition. The raw plant materials may be dried to reduce water content. Drying may occur by a number of different means, such as, for example, air-dried, oven-dried, rotary evaporated under vacuum or lyophilized. The CGRP plant can also be in the form of a liquid or solid extract. The solid extract is, for example, a lyophilized extract or a concentrated and dried form of the liquid extract. In an embodiment of the disclosure, the raw plant materials are collected from any plant that increases the expression of CGRP. In certain embodiments, the raw materials collected from the CGRP plant are ground into small sized particles. Methods and processes commonly used and known in the art for preparing a plant extract are utilized. In particular, the methods described in International Application Publication Nos. WO 03/079816; WO 04/014958; and WO 04/014404, all of which are incorporated herein by reference. As is understood, modifications and adaptations of the extraction processes are possible, particularly during a scale-up to larger volumes for production.

Briefly, in one embodiment, the plant extract that stimulates expression of CGRP may be obtained by distilling the raw plant materials with a stripping agent. The stripping agent may be a liquid that is miscible, immiscible, or partially miscible with the desired extract from the plant. Suitable stripping agents include, but are not limited to, water; alcohols (such as methanol, ethanol, propanol, butanol and the like); glycols; ethers (such as diethyl ether, dipropyl ether, and the like); esters (such as butyl acetate, ethyl acetate, and the like); ketones (such as acetone, ethyl methyl ketone, and the like); dimethyl sulfoxide; acetonitrile; other organic solvents; and combinations thereof. In one embodiment, the stripping agent is immiscible with the desired plant extract (e.g., essential oil). In one embodiment, the stripping agent is water. In another embodient, the plant extract is obtained by steam distillation. The CGRP plant extract may be collected by phase separation from the stripping agent. It is believed that the stripping agent increases the overall vapor pressure of a distillation system for obtaining the extract and thereby reduces the boiling point of the desired product, i.e., the CGRP plant extract (or for example, the essential oil).

In other embodiments of the disclosure, the CGRP plant extract is obtained by solvent extraction, such as for example, an organic solvent extraction. Briefly, the organic solvent extraction method involves washing and extracting the raw materials, which may be whole, cut up, minced, or ground into small particle sizes, with an organic solvent. Non-limiting examples of organic solvents include methanol, ethanol, isopropanol, dichloromethane, chloroform, hexane, xylene, and petroleum ether. An extraction machine may be used for organic solvent extraction as is well known and commonly performed in the art. The raw materials are pushed in the extraction machine by a thruster, which slowly moves the plant raw materials forward. Organic solvent (e.g., ethanol) may be added into the machine through a solvent inlet at the top of a waste discharge outlet. Due to the difference in gravity and equilibrium, the solvent flows toward the raw material inlet, soaks the materials and flows out from the opposite side of the solvent inlet. Since the plant materials and the solvent move in opposite directions against each other, the plant materials are constantly immersed in a solution that contains a low-concentration of extract. As a result of equilibrium, high yield of plant constituent(s) may be achieved by continuously extracting the plant material against the low-concentration solution.

An extraction time suitable to extract the plant constituents is typically between about 1 to about 10 hours, and in a more specific range, between about 2 to about 8 hours, or between about 3 hours to about 6 hours. The temperature of extraction is generally between about 30° C. to about 100° C., between about 40° C. to about 70° C., and between about 50° C. to about 60° C. The collected extract is then fine-filtered to remove debris, and may be used directly, or is concentrated, for example by distilling the solvent or by other conventional processing. The solution of extract actives may be rotary evaporated under vacuum or lyophilized. A typical extract actives content is above about 25% or above about 50%, and the extract can also be provided an essential oil or a concentrate having a semi-solid or solid consistency.

Similarly, aqueous-organic solvent extraction involves initially collecting raw materials from the CGRP expression stimulating plants, which may be whole or ground into small particles. The ground plant material is soaked in aqueous solution that is acidic or alkaline, depending on the solubility and stability of the desired extract under acidic or alkaline (basic) conditions. For extraction under acidic conditions, an acid such as hydrochloric acid or sulfuric acid is added to water, e.g., at a concentration of about 3% (w/v). For extraction under alkaline conditions, an alkali such as sodium hydroxide or sodium carbonate is added to water. The extraction time and temperature of extraction are typically similar to that used in the organic solvent extraction method described above.

The extract is then collected and fine-filtered to remove undesired debris. Alkaline agents (e.g., ammonia) or acidifying agents (e.g., sulfuric acid) may be added to the extract to neutralize the solution by adjusting the pH, depending on the acidity or alkalinity of the collected extract. The aqueous extract may be used directly, concentrated or dried. Alternatively, organic solvent may then be added to the neutralized solution to transfer the extract from an aqueous phase to an organic phase. Examples of such organic solvents include, but are not limited to, ethanol, isopropanol, butanol, pentanol, hexanol and xylene. The extract comprising the transferred extract actives dissolved in organic solvent may be used directly as an essential oil or a concentrate, or dried by a number of different means, such as, for example, air-dried, oven-dried, rotary evaporated under vacuum or lyophilized to a semi-solid or solid consistency.

It should also be noted that different plants containing different constituents can be mixed and extracted together with any of the CGRP plants. This process of mixed extraction can rather, in one embodiment, be used for extracting those plants containing constituents with similar solubility as the CGRP plants in the solvent used for extraction, such as ethanol. The mixture of extracts can be concentrated and stored in an appropriate solvent.

In another embodiment, the CGRP plant extract as used herein, also includes "synthetic" extracts, i.e., various combinations of known plant components and/or constituents that are combined to substantially mimic the composition and/or activity of a CGRP plant extract of natural origin. The synthetic extracts have substantially the same number of active components as a natural CGRP plant material. The numerical incidence of actives corresponding to the synthetic extracts and the natural plant material may also be described in terms of "percent commonality." The synthetic extract has about 50 percent or more commonality to the chemical composition of a plant or natural extract. In other words, the synthetic extract has about 50 percent or more of the active ingredients found in the plant or a natural extract. More preferably, the chemical composition of the synthetic extract has about 70 percent or more commonality to the chemical composition of a plant or a natural extract. Optimally, a synthetic extract has about 90 percent or more commonality to the chemical composition of a plant or a natural extract.

A further embodiment of the disclosure is directed to CGRP compositions comprising an effective amount or an amount sufficient to reduce the appearance or severity of fine lines or wrinkles, relax muscles, block muscle cell contraction, or block acetylcholine from binding the Ach receptor in a given area of skin when topically applied thereto. The above amounts refer to an "active amount" of a CGRP or a CGRP plant. An "amount effective," an "effective amount," or "sufficient amount" to provide a particular anti-aging benefit to the skin refers to the "active amount" of a CGRP or a CGRP plant required to provide a clinically measurable or visual improvement in the particular manifestation of skin aging when applied for a time sufficient to provide a clinically measurable or visual improvement in the particular manifestation of skin aging.

In another embodiment, the CGRP ingredient is in an amount effective or sufficient to result in reduced or diminished wrinkles or the blockage of muscle contractions or the ACh signaling pathway, by, for example, preventing the release of ACh or binding of ACh to its receptor. The amount will vary depending upon the type of agent and the nature and level of the desired effect. The CGRP ingredient will typically be present from about 0.001 wt % to about 20 wt %, more preferably from about 0.01 wt % to about 5 wt %, and most preferably from about 0.1 wt % to about 2.5 wt %, based on the total weight of the composition. As is understood by the skilled artisan, the CGRP ingredient is combined with a carrier, a vehicle, or a diluent to form the CGRP composition, which is in a specific embodiment, a topical CGRP composition.

In one embodiment, the CGRP composition of the disclosure comprising CGRP ingredients, may have a pH that is comparable for its intended use. For example, a moisturizer may have a pH in the neutral or alkaline range; whereas, an exfoliating product may have a pH in the acidic range. Regardless, the pH range would be compatible both cosmetically and physiologically, without any detrimental or undesirable effects. In certain embodiments, the pH of the composition will be acidic, i.e., less than 7.0, a pH ranging from about 2 to about 7, or from a pH of about 3.5 to about 5.5. Other embodiments might require that the composition has a pH ranging from about 6.5 to about 10.

Another embodiment of the present disclosure provides compositions in an effective amount of compositions, including a CGRP ingredient to treat, reverse, ameliorate and/or inhibit signs of skin damage or skin aging. The disclosed CGRP composition may also be used as a prophylactic by applying to as of yet wrinkled skin, i.e., non-wrinkled skin. Benefits of the instant composition described herein include without limitation, the following:
  (a) treatment, reduction, and/or inhibition of fine lines or wrinkles,
  (b) reduction of skin pore size,
  (c) improvement in skin thickness, plumpness, and/or tautness;
  (d) improvement in skin suppleness and/or softness;
  (e) improvement in skin tone, radiance, and/or clarity;
  (f) improvement in procollagen and/or collagen production;
  (g) improvement in maintenance and remodeling of elastin;
  (h) improvement in skin texture and/or promotion of retexturization;
  (i) improvement in skin barrier repair and/or function;
  (j) improvement in appearance of skin contours;
  (k) restoration of skin luster and/or brightness;

(l) replenishment of essential nutrients and/or constituents in the skin;
(m) improvement of skin appearance decreased by aging and/or menopause;
(n) improvement in skin moisturization and/or hydration;
(o) increase in and/or preventing loss of skin elasticity and/or resiliency;
(p) treatment, reduction, and/or prevention of skin sagging; and/or
(q) treatment, reduction, and/or prevention of discoloration of skin.

Another embodiment relates to the use of the inventive topical CGRP composition to treat or reduce the appearance of discoloration of skin which includes discrete pigmentation. This type of pigmentation is commonly known as pigment spots or "age spots," and mottled pigmentation. Discrete pigmentation are distinct uniform areas of darker pigment and may appear as brown spots or freckles on the skin. Mottled pigmentation are dark blotches that are larger and more irregular in size and shape than discrete pigmentation. Areas of mottled pigmentation tend to become darker with sun exposure.

In a further embodiment, the CGRP composition may be useful in treating aged or damaged skin. Elasticity of the skin refers to the springiness and resilience of skin's ability to regain its original shape and size after deformation. Elasticity of the skin may be evaluated by a pinch test that can either cause deformation by stretching or squeezing the skin. The topical CGRP composition of the disclosure may be useful in treating skin that has reduced elasticity.

In practice, one embodiment of the disclosure relates to the CGRP compositions that are topically applied to skin in need of treatment. That is, skin which suffers from a deficiency or loss in any of the foregoing attributes or which would otherwise benefit from improvement in any of the foregoing skin attributes. Generally, the improvement in the condition and/or aesthetic appearance is selected from the group consisting of: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation; and any combinations thereof.

One application of such a topical CGRP composition is an anti-wrinkle composition. The anti-wrinkle composition is applied to, for example, skin that has fine lines, wrinkles, creases, or skin folds, such as for example, those found on the forehead and around the eyes and mouth. The CGRP composition is in an amount effective to relax the muscles underneath the top layer of skin. The CGRP composition is also in an amount effective to inhibit muscle contraction. The topical composition may be in the form of a lotion, a cream, an ointment, a gel, a serum, an emulsion, a spray, an aerosol, or a stick. Depending on the application, the CGRP ingredient may be useful in a skin care, make up or cosmetic composition, such as for example, a foundation, a powder, and the like, for topical application.

In one embodiment, methods for treating fine lines and wrinkles comprise topically applying the inventive CGRP compositions to the skin of an individual in need thereof, i.e., having fine lines, deep creases, wrinkles, skin folds, and the like as a result of aging skin. A further embodiment is directed to a method of treating where a topical CGRP composition comprising an effective amount of a CGRP ingredient or combinations thereof in a physiologically- or cosmetically-acceptable vehicle is directly applied to the affected area of skin having fine lines and/or wrinkles for a period of time in order to reduce, ameliorate or reverse the severity or appearance of the dermatological signs of aging, including, for example, fine lines, wrinkles, creases, furrows, and the like. This method is also particularly useful for treating signs of skin photoaging and intrinsic aging.

Due to intrinsic or extrinsic factors, oftentimes people feel the need to avoid the reality of aging as projected by fine lines and wrinkles. In so doing, the compounds or compositions of the disclosure may be applied to areas which are known to produce fine lines and wrinkles and yet have not materialized. A further embodiment relates to CGRP compositions of the disclosure used prophylactically to inhibit or delay the formation of new or the development of existing fine lines and/or wrinkles that result from continuous or frequent muscle contraction. For example, the disclosed CGRP compositions comprising a CGRP extract may be used prophylactically on skin that is anticipated to have fine lines and wrinkles. Fine lines generally begin to appear in women 25 years old or older; however, they may appear earlier if the skin was exposed to a lot of sun without protection, and also depends in part on genetics. This method of the disclosure may be employed prophylactically to forestall aging including in patients that have not manifested signs of skin aging, most commonly in individuals under 25 years of age. The method may also reverse or treat signs of aging once manifested as is common in patients over 25 years of age. Thus, if women anticipate that they will get fine lines and wrinkles in the near future, they should utilize the inventive CGRP composition in order to delay the production of fine lines and wrinkles.

The CGRP compositions of the disclosure are also useful for treating thin skin by topically applying the composition to thin skin of an individual in need thereof. "Thin skin" is intended to include skin that is thinned due to chronological aging, menopause, or photo-damage. In some embodiments, the treatment is for thin skin in men, whereas other embodiments treat thin skin in women, pre-menopausal or postmenopausal, as it is believed that skin thins differently with age in men and women, and in particular in women at different stages of life.

In certain embodiments the compounds, compositions, and methods of the disclosure are directed to the treatment and/or amelioration of fine lines and/or wrinkles of the skin. In this particular embodiment, the compositions are applied to skin in need of treatment, by which is meant skin having wrinkles and/or fine lines. They are applied directly to the fine lines and/or wrinkles. The compositions and methods are suitable for treating fine lines and/or wrinkles on any surface of the skin, including without limitation, the skin of the hands, arms, legs, neck, chest, and face, including the forehead and around the eyes and mouth. The effect of a CGRP composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin).

The disclosed CGRP composition will typically be applied to the skin one, two, three times or more daily or weekly, for as long as is necessary to achieve desired anti-aging results. The treatment regimen may comprise daily application for at least one week, at least two weeks, at least four weeks, at least eight weeks, or at least twelve weeks. Chronic treatment regimens are also contemplated.

A CGRP composition is topically applied to an "individual in need thereof," by which is meant an individual that stands to benefit from reducing visible signs of skin damage or aging. Such a composition is then topically applied to an affected area of skin of an individual in need thereof, i.e., having damaged or aged skin as portrayed by fine lines, wrinkles and the like, and left to remain on the affected area in an amount and for a period of time effective for improving the condition and aesthetic appearance of skin.

In another embodiment, the CGRP composition may be formulated in a variety of product forms, such as, for example, a lotion, a cream, a serum, a spray, an aerosol, a cake, an ointment, an essence, a gel, a paste, a patch, a powder, a pencil, a towelette, a mask, a stick, a foam, a mousse, a semi-solid, an elixir, a concentrate, and the like, particularly for topical administration or application. More specifically, the inventive topical CGRP composition is formulated as a lotion, a cream, an ointment, a serum, or a gel.

A further embodiment is directed to CGRP compositions comprising a cosmetically- and/or physiologically acceptable carrier, vehicle, or diluent. Such carriers, vehicles, or diluents include, but not limited to, any known in the art suitable for application to skin and may include water (e.g., deionized water); vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicones, dimethicones, dimethicone cross-polymer, polysiloxanes and their derivatives, preferably organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing.

More specifically, the carrier, vehicle, or diluent may comprise an aqueous phase, an oil phase, an alcohol, a silicone phase or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant.

The oil phase of the emulsion may have one or more organic compounds, including emollients; humectants (such as butylene glycol, propylene glycol, methyl gluceth-20, and glycerin); other water-dispersible or water-soluble components including thickeners such as veegum or hydroxyalkyl cellulose; gelling agents, such as high molecular weight polyacrylic acid, i.e. CARBOPOL® 934; and mixtures thereof. The emulsion may have one or more emulsifiers capable of emulsifying the various components present in the composition.

The compounds suitable for use in the oil phase include without limitation, vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like. Suitable hydrophobic hydrocarbon oils may be saturated or unsaturated, have an aliphatic character and be straight or branched chained or contain alicyclic or aromatic rings. The oil-containing phase may be composed of a singular oil or mixtures of different oils.

Hydrocarbon oils include those having 6-20 carbon atoms or more specifically, 10-16 carbon atoms. Representative hydrocarbons include decane, dodecane, tetradecane, tridecane, and $C_{8-20}$ isoparaffins. Paraffinic hydrocarbons are available from Exxon under the ISOPARS™, and from the Permethyl Corporation. In addition, $C_{8-20}$ paraffinic hydrocarbons such as $C_{12}$ isoparaffin (isododecane) manufactured by the Permethyl Corporation having the tradename Permethyl 99A™ are also contemplated to be suitable. Various commercially available $C_{16}$ isoparaffins, such as isohexadecane (having the tradename Permethyl®) are also suitable. Examples of preferred volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals. A representative hydrocarbon solvent is isododecane.

The oil phase may comprise of one or more waxes. The wax may provide for a smooth feel, as well as for a structural component. Non-limiting examples of waxes useful in the inventive composition include rice bran wax, carnauba wax, ouricurry wax, candelilla wax, montan waxes, sugar cane waxes, ozokerite, polyethylene waxes, Fischer-Tropsch waxes, beeswax, microcrystaline wax, silicone waxes, fluorinated waxes, and the like, or any combination thereof.

Non-limiting emulsifiers included emulsifying waxes, emulsifying polyhydric alcohols, polyether polyols, polyethers, mono- or di-ester of polyols, ethylene glycol mono-stearates, glycerin mono-stearates, glycerin di-stearates, silicone-containing emulsifiers, soya sterols, fatty alcohols such as cetyl alcohol, acrylates, fatty acids such as stearic acid, fatty acid salts, and mixtures thereof. Certain specific embodiments include emulsifiers selected from: soya sterol, cetyl alcohol, stearic acid, emulsifying wax, acrylates, silicone containing emulsifiers and mixtures thereof. Other specific emulsifiers that can be used in the composition of the present disclosure include, but are not limited to, one or more of the following: $C_{10-30}$ alkyl acrylate crosspolymer; Dimethicone PEG-7 isostearate, acrylamide copolymer; mineral oil; sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the *INCI Ingredient Dictionary and Handbook* 11th Edition 2006, the disclosure of which is hereby incorporated by reference.

A further embodiment relates to emulsifiers used in the compositions of the disclosure in an amount from about 0.001% to about 10% by weight, in particular in an amount from about 0.01% to about 5% by weight, and more specifically, from about 0.1% to about 3% by weight of the total composition.

In yet another embodiment, the oil phase may comprise one or more volatile and/or non-volatile silicone oils. Volatile silicones include, but are not limited to, cyclic and linear volatile dimethylsiloxane silicones. In one embodiment, the volatile silicones include cyclodimethicones, such as, tetramer (D4), pentamer (D5), and hexamer (D6) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones are available from Dow Corning under the name Dow Corning 200® Fluid and have viscosities ranging from 0.65 to 600,000 centistokes or higher. Suitable non-polar, volatile liquid silicone oils as well as volatile silicone materials are disclosed in U.S. Pat. No. 4,781,917 and Todd et al., "Volatile Silicone Fluids for Cosmetics", *Cosmetics and Toiletries*, 91:27-32 (1976), herein incorporated by reference in their entirety. Linear volatile silicones generally have a viscosity of less than about 5 centistokes at 25° C., whereas the cyclic silicones have viscosities of less than about 10 centistokes at 25° C. Non-limiting examples of useful volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane, to name a few.

Non-volatile silicone oils generally comprise polyalkylsiloxanes, polyarylsiloxanes, polyalkylarylsiloxanes, or mixtures thereof. Polydimethylsiloxanes are particularly useful non-volatile silicone oils. The non-volatile silicone oils useful in the instant composition have a viscosity ranging from about 10 to about 60,000 centistokes at 25° C., from about 10 to about 10,000 centistokes, and more particularly from about 10 and about 500 centistokes; and a boiling point greater than 250° C. at atmospheric pressure. Non limiting examples include dimethyl polysiloxane (dimethicone), phenyl trimethicone, and diphenyldimethicone.

The volatile and non-volatile silicone oils may optionally be substituted with various functional groups, such as but not limited to, alkyl, aryl, amine groups, vinyl, hydroxyl, haloalkyl groups, alkylaryl groups, acrylate groups, and the like, to name a few.

Another embodiment of the disclosure is directed to the composition comprising a water-in-silicone emulsion that may be emulsified with a nonionic surfactant (emulsifier) such as, for example, polydiorganosiloxane-polyoxyalkylene block copolymers, or any other suitable water-in-silicone emulsifiers, including any of those described in U.S. Pat. Nos. 4,122,029 and 6,685,952, the disclosures of which are hereby incorporated by reference. These emulsifiers generally comprise a polydiorganosiloxane backbone, typically polydimethylsiloxane, having side chains comprising -(EO)$_m$— and/or —(PO)$_n$— groups, where EO is ethyleneoxy and PO is 1,2-propyleneoxy, the side chains being typically capped or terminated with hydrogen or lower alkyl groups (e.g., $C_{1-6}$, typically $C_{1-3}$). Commercially available water-in-silicone emulsifiers include those from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWET series of emulsifiers sold by OSI Specialties (Danbury, Conn.).

Non-limiting examples of water-in-silicone emulsifiers include dimethicone PEG 10/15 crosspolymer, dimethicone copolyol, cetyl dimethicone copolyol, PEG-15 lauryl dimethicone crosspolymer, laurylmethicone crosspolymer, cyclomethicone and dimethicone copolyol, dimethicone copolyol (and) caprylic/capric triglycerides, polyglyceryl-4 isostearate (and) cetyl dimethicone copolyol (and) hexyl laurate, and dimethicone copolyol (and) cyclopentasiloxane. Specific examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), dimethicone PEG-10/15 crosspolymer (trade name KSG-210, Shin-Etsu), and dimethicone PEG-7 isostearate.

Another embodiment of the disclosure is directed to water-in-silicone emulsifiers. These are present in the inventive composition in an amount from about 0.001% to about 10% by weight, in particular in an amount from about 0.01% to about 5% by weight, and more specifically, below 1% by weight of the total composition disclosed herein.

In yet a further embodiment of the disclosure, the aqueous phase of the emulsion may include one or more additional solvents, including, for example, lower alcohols, such as ethanol, isopropanol, and the like. The volatile solvent may also be a cosmetically acceptable ester such as butyl acetate or ethyl acetate; ketones such as acetone or ethyl methyl ketone; or the like.

One embodiment of the disclosure is directed to an oil-containing phase of the inventive disclosure. The oil-containing phase is generally in an amount ranging from about 10% to about 99%, from about 20% to about 85%, and more specifically from about 30% to about 70% by weight based on the total weight of the emulsion, and the aqueous phase will correspondingly be in an amount ranging from about 1% to about 90%, from about 5% to about 70%, and more particularly, from about 20% to about 60% by weight of the total emulsion in the inventive disclosure. The aqueous phase will typically comprise of an amount ranging from about 25% to about 100%, and more typically from about 50% to about 95% by weight of water.

The disclosed compositions may include liposomes in another embodiment. The liposomes may comprise of other additives or substances and/or may be modified to more specifically reach or remain at a site following administration. For example, the liposomes may assist in delivering the CGRP or plant containing CGRP to the skin having fine lines or wrinkles that need treatment.

In yet another embodiment of the disclosure, the inventive composition may optionally include other actives and excipients useful in various applications, such as those found in cosmetics, skin or personal care products, including, but not limited to, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, depigmenting agents, hypopigmenting agents, preservatives (e.g., DMDM Hydantoin/Iodopropynylbutylcarbonate), stabilizers, pharmaceutical agents, photostabilizing agents, neutralizers (e.g., triethanolamine) and mixtures thereof. In addition to the foregoing, the compositions of the disclosure may contain any other compound for the treatment of skin disorders or conditions that do not detrimentally affect the primary purpose of reducing the appearance of fine lines or wrinkles. For example, in one embodiment, the inventive composition may additional have an ultraviolet filter as found in a sunblock to provide a dual purpose composition, i.e., an anti-wrinkle and UV protecting composition.

A further embodiment of the disclosure relates to the inventive compositions additionally comprising colorants to produce a cosmetic composition. Non-limiting colorants useful in the inventive cosmetic composition include organic pigments, inorganic pigments, goniochromatic pigments, holographic glitters, and pearlescent agents. Suitable inorganic pigments include, but are not limited to, titanium oxide, zirconium oxide and cerium oxide, as well as zinc oxide, iron oxide, chromium oxide and ferric blue. While, suitable organic pigments include barium, strontium, calcium, and aluminium lakes and carbon black. Suitable pearlescent agents include mica coated with titanium oxide, with iron oxide, or with natural pigment.

Depending on the application, the inventive composition may additionally comprise various fillers and components. Fillers may be present in an amount ranging from about 0 weight % to about 20 weight % based on the total weight of the composition or from about 0.1 weight % to about 10 weight %. Suitable fillers include without limitation silica, treated silica, talc, zinc stearate, mica, kaolin, nylon powders such as Orgasol™ (Arkema Inc.; Philadelphia, Pa.), polyethylene powder, Teflon™ (Dupont; Parkersburg, W. Va.), starch, boron nitride, copolymer microspheres such as Expancel™ (AkzoNobel; Sundsvall, Sweden), Polytrap™ polymers (AMCOL Health & Beauty Solutions Inc.; Lafayette, La.) and silicone resin microbeads (Tospearl™; Momentive Performance Materials Inc.; Albany, N.Y.), and the like.

In one embodiment of the disclosure, the inventive compositions may include additional skin actives. These actives include, but are not limited to, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, salicylic acid or salicylates, thiodipropionic acid or esters thereof, anti-aging agents, anti-discoloration agents and advanced glycation end-product (AGE) inhibitors. Depending on the application, the inventive disclosure may also include such skin actives which work in conjunction with the CGRP composition.

One specific embodiment, the composition may comprise at least one additional botanical, such as, for example, a botanical extract, an essential oil, or the plant itself. Suitable botanicals include, without limitation, extracts from aloe vera, plants that lighten skin, anti-aging plants, or combinations thereof.

Another embodiment is directed to the inventive composition comprising additional active ingredients having anti-aging benefits, as it is contemplated that synergistic improvements may be obtained with such combinations. Exemplary anti-aging components include, without limitation, botanicals (e.g., *Butea Frondosa* extract); thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few.

Non-limiting retinoids include retinoic acid (e.g., all-trans or 13-cis) and derivatives thereof, retinol (Vitamin A) and esters thereof, such as retinol palmitate, retinol acetate and retinol propionate, and salts thereof.

In another embodiment, the topical compositions of the present disclosure may also include one or more of the following: a skin penetration enhancer, an emollient, a skin plumper, an optical diffuser, a sunscreen, an exfoliating agent, and an antioxidant.

Further embodiments relate to the inventive compositions with an emollient. Emollients are known in the art to provide functional benefits of enhancing skin smoothness and reducing the appearance of fine lines and coarse wrinkles, in addition to providing a composition with a satiny feel. Non-limiting examples include isopropyl myristate, petrolatum, isopropyl lanolate, silicones (e.g., methicone, dimethicone), oils, mineral oils, fatty acid esters, cetyl ethylhexanoate, $C_{12-15}$ alkyl benzoate, isopropyl isostearate, diisopropyl dimer dillinoeate, or any mixtures thereof. The emollient may be present in a specific embodiment from about 0.1 weight % to about 50 weight % of the total weight of the inventive composition.

Another embodiment of the instant disclosure is directed to a skin plumper that serves as a collagen enhancer to skin. An example of a suitable, and particularly useful, skin plumper is palmitoyl oligopeptide. Other skin plumpers include but are not limited to collagen and/or other glycosaminoglycan (GAG) enhancing agents. When present, the skin plumper may be present in an amount ranging from about 0.1 weight % to about 20 weight % of the total weight of the composition.

In yet a further embodiment, an optical diffuser may be included in the inventive composition. An optical diffuser is a particle that changes the surface optometrics of skin, resulting in a visual blurring and softening of, for example, lines and wrinkles. Non-limiting examples of optical diffusers that can be used in the present disclosure include boron nitride, mica, nylon, polymethylmethacrylate (PMMA), polyurethane powder, sericite, silica, silicone powder, talc, Teflon®, titanium dioxide, zinc oxide, or any mixtures thereof. The optical diffuser may be present in an amount ranging from about 0.01 weight % to about 20 weight % of the total weight of the composition.

Another embodiment of the disclosure is directed to the addition of a sunscreen for protecting the skin from damaging ultraviolet rays. Non-limiting examples of sunscreens are those with a broad range of UVB and UVA protection, such as octocrylene, avobenzone (Parsol® 1789), octyl methoxycinnamate, octyl salicylate, oxybenzone, homosylate, benzophenone, camphor derivatives, zinc oxide, titanium dioxide, and the like. When present, the sunscreen may comprise from about 0.01 weight % to about 70 weight % of the total composition.

Suitable exfoliating agents for use in certain embodiments of the inventive disclosure include, but are not limited to, alpha-hydroxyacids, beta-hydroxyacids, oxaacids, oxadiacids, and their derivatives such as esters, anhydrides and salts thereof. Non-limiting hydroxy acids include glycolic acid, lactic acid, malic acid, tartaric acid, citric acid, 2-hydroxyalkanoic acid, mandelic acid, salicylic acid and derivatives thereof. A particularly useful exfoliating agent is glycolic acid which may assist with the anti-aging benefits of the disclosed composition. When present, the exfoliating agent may be in an amount ranging from about 0.1 weight % to about 80 weight % of the composition.

As is understood in the art, an antioxidant functions, among other things, to scavenge free radicals from skin to protect the skin from environmental stressors which are known to prematurely age skin, or at least give the appearance of mature skin with fine lines and wrinkles. Not only are antioxidants useful in protecting the skin from such stressors, but also, as previously explained, they protect against degradation of ingredients, particularly, for example, the non-ionic unsaturated fatty alcohol of the inventive disclosure. Non-limiting examples of antioxidants that may be used in the present compositions include compounds having phenolic hydroxy functions, such as ascorbic acid and its derivatives/esters; alpha-hydroxyacids; beta-carotene; catechins; curcumin; ferulic acid derivatives (e.g. ethyl ferulate, sodium ferulate); gallic acid derivatives (e.g., propyl gallate); lycopene; reductic acid; rosmarinic acid; tannic acid; tetrahydrocurcumin; tocopherol and its derivatives (e.g., tocopheryl acetate); uric acid; antioxidants that have one or more thiol functions (—SH), in either reduced or non-reduced form, including glutathione, lipoic acid, thioglycolic acid, and other sulfhydryl compounds. The antioxidant described herein may be, for example, inorganic, including but not limited to bisulfites, metabisulfites, sulfites, or other inorganic salts and acids containing sulfur. Compositions of the present disclosure may comprise an antioxidant or several antioxidants in an amount ranging from about 0.001 weight % to about 10 weight % and from about 0.01 weight % to about 5 weight % of the total weight of the composition.

As the skilled practitioner understands, other conventional additives may be included in the inventive composition depending on the intended us. For example, the inventive composition may include, but is not limited to: vitamins, such as tocopherol and ascorbic acid; vitamin derivatives such as ascorbyl monopalmitate; thickeners such as hydroxyalkyl cellulose; gelling agents; structuring agents such as bentonite, smectite, magnesium aluminum silicate and lithium magnesium silicate; metal chelating agents such as EDTA; pigments such as zinc oxide and titanium dioxide; colorants; emollients; and humectants.

It is ideal that the composition be essentially free of components having a strong oxidizing potential, including for example, organic or inorganic peroxides. By "essentially free of" these components is meant that the amounts present are insufficient to have a measurable impact on CGRP expression by CGRP, plants expressing CGRP, or for example, extracts of *Erythrina flabelliformis, Sophora tomentosa*, or combinations thereof. In some embodiments, the insufficient amounts will be less than 0.0001% by weight of the amount of extracts of *Erythrina flabelliformis, Sophora tomentosa*, or combinations thereof.

The contents of all patents, patent applications, published PCT applications and articles, books, references, reference manuals and abstracts cited herein are hereby incorporated by reference in their entirety to more fully describe the state of the art to which the disclosure pertains.

As various changes may be made in the above-described subject matter without departing from the scope and spirit of the present disclosure, it is intended that all subject matter contained in the above description, or defined in the appended claims, be interpreted as descriptive and illustrative of the present disclosure. Many modifications and variations of the present disclosure are possible in light of the above teachings.

EXAMPLES

The following examples further describe and demonstrate embodiments within the scope of the present disclosure. The examples are given solely for the purpose of illustration and is not to be constructed as limitations of the present disclosure, as many variations thereof are possible without departing from the spirit and scope of the disclosure. The following exemplary compositions and methods are given by way of illustration only and in no way intended to be limiting to the scope of invention.

Example 1

CGRP Expression Assay

The CGRP assay was used to measure the levels of expression found in ingredients that may be useful in CGRP compositions. Briefly, the CGRP assay was performed as follows.

PC-12 cells (ATCC; Manassas, Va.) were cultured in 6-well tissue culture plates (Falcon), at a seeding density of $5\times10^4$ cells/ml at 37° C. and 5% $CO_2$ in F12K culture medium supplemented with 15% Horse Serum (HS), 2.5% Fetal Bovine Serum (FBS), 1% penicillin/streptomycin, 0.5% BSA, and 100 ng/ml of NGF. Cells were cultured for 10 days, then cells were exposed to the test article or control vehicle diluted in 750 microliters of culture medium at the appropriate concentration and incubated for 24 hours. The final weight % of the test article ranged from about 0.0001% to about 0.1%. The resulting percent changes over the positive control were all statistically significant (p<0.05) ranging from about 21% to about 300%. The amount of CGRP secreted by the PC-12 cells was quantitated using a commercial CGRP ELISA kit purchased from SPI Bio (France), by following the manufacturer's protocol. The amount of CGRP in the samples were calculated using a standard curve and the percent change in CGRP following exposure to the test articles was calculated relative to the positive control.

Example 2

Exemplary CGRP Compositions

Compositions comprising a CGRP ingredient as described herein for topical application to skin having fine lines, wrinkles, deep folds, and the like due to aging and/or diseases or disorders that cause skin to have the appearance of aging skin are provided in Table 1.

The CGRP ingredient utilized and described in Table 1 includes any of the described CGRP compounds, CGRP natural ingredients, or combinations thereof, such that the total CGRP ingredient in weight percent is indicated.

TABLE 1

| | Composition: | | | |
|---|---|---|---|---|
| | 1 | 2 | 3 | 4 |
| Components | Weight % | | | |
| CGRP ingredient | 0.3 | 0.03 | 0.01 | 0.005 |
| Acrylates/$C_{10\text{-}30}$ Alkyl Acrylate Crosspolymer | 1 | 1 | 1 | 1 |
| Cetyl Ethylhexanoate | 10 | 10 | 10 | 10 |
| $C_{12\text{-}15}$ Alkyl Benzoate | 3.9 | 3.9 | 3.9 | 3.9 |
| Isopropyl Isostearate | 3 | 3 | 3 | 3 |
| Diisopropyl dimer dillinoleate | 0.1 | 0.1 | 0.1 | 0.1 |
| Tocopheryl acetate | 0.5 | 0.5 | 0.5 | 0.5 |
| Butylene glycol | 2 | 2 | 2 | 2 |
| Propylene glycol | 1 | 1 | 1 | 1 |
| Dimethicone PEG-7 isostearate | 0.5 | 0.5 | 0.5 | 0.5 |
| Methyl gluceth-20 | 0.5 | 0.5 | 0.5 | 0.5 |
| Triethanolamine | 1 | 1 | 1 | 1 |
| Acrylates/acrylamide copolymer/mineral oil | 1.5 | 1.5 | 1.5 | 1.5 |
| DMDM Hydantoin/Iodopropynylbutylcarbonate | 0.4 | 0.4 | 0.4 | 0.4 |
| Deionized water | q.s. | q.s. | q.s. | q.s. |
| Total: | 100 | 100 | 100 | 100 |

These compositions are believed to be effective to treat, reverse, and/or ameliorate signs of skin aging. Specifically, the CGRP compositions are believed to reduce the appearance of fine lines and wrinkles in the skin. The CGRP compositions of Table 1 may be applied to skin in need of treatment, by which is meant skin in need of an anti-aging benefit, and in particular skin having wrinkles and/or fine lines. The CGRP compositions may be applied directly to the fine lines and/or wrinkles. The exemplary compositions may be applied to treat, reverse, ameliorate and/or prevent fine lines and/or wrinkles on any surface of the skin, including without limitation, the skin of the face, neck, and/or hands.

The cosmetic compositions are applied to the skin having fine lines and/or wrinkles one, two or three times daily for as long as is necessary to achieve the desired anti-aging results. The treatment regiment may comprise daily application for at least one week, at least two weeks, at least four weeks, at least eight weeks, or at least twelve weeks. Alternatively, the exemplary cosmetic compositions may be used in chronic treatment of the skin, fine line and/or wrinkle. Moreover, the CGRP compositions may be applied to skin that is prone to wrinkles as a prophylactic agent to reduce the appearance of fine lines or wrinkles.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for reducing wrinkles and/or fine lines of an individual in need thereof comprising: topically applying a composition comprising an extract of *Derris Scandens Benth*, in a cosmetically acceptable vehicle, to a wrinkle and/or fine line on said individual's skin for a time sufficient to reduce the severity of said wrinkle and/or fine line.

2. The method of claim 1, wherein the composition comprises 0.1 weight % to about 10 weight % of said extract.

* * * * *